United States Patent
Chuang

(10) Patent No.: US 12,338,276 B2
(45) Date of Patent: Jun. 24, 2025

(54) FIBRONECTIN TYPE III DOMAIN-BASED PROTEIN AND APPLICATION THEREOF

(71) Applicant: NATIONAL CHENG KUNG UNIVERSITY, Tainan (TW)

(72) Inventor: Woei-Jer Chuang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 17/977,247

(22) Filed: Oct. 31, 2022

(65) Prior Publication Data
US 2024/0209064 A1    Jun. 27, 2024

(30) Foreign Application Priority Data
Sep. 16, 2022 (TW) .................................. 111135255

(51) Int. Cl.
*C07K 14/78* (2006.01)
*A61K 38/00* (2006.01)
*A61P 9/10* (2006.01)

(52) U.S. Cl.
CPC ................ *C07K 14/78* (2013.01); *A61P 9/10* (2018.01); *A61K 38/00* (2013.01)

(58) Field of Classification Search
None
See application file for complete search history.

(56) References Cited

PUBLICATIONS

Gilbreth et al. "Stabilization of the third fibronectin type III domain of human tenascin-C through minimal mutation and rational design" Protein Engineering, Design & Selection 27:411-418. (Year: 2014).*

* cited by examiner

*Primary Examiner* — Sudhakar Katakam
*Assistant Examiner* — Zachary J Miknis
(74) *Attorney, Agent, or Firm* — troutman pepper locke; Tim Tingkang Xia, Esq.

(57) ABSTRACT

The present invention provides a protein, and the protein includes a 10th human fibronectin type III domain and has a first mutation at an amino acid residue with a cysteine residue and a second mutation at another amino acid residue with another cysteine residue, wherein the first mutation and the second mutation take place at a region of the 10th human fibronectin type III domain other than a loop FG so that a disulfide bond is formed between the cysteine residue formed by the first mutation and the cysteine residue formed by the second mutation.

16 Claims, 4 Drawing Sheets
Specification includes a Sequence Listing.

Protein C7-NM

US 12,338,276 B2

FIBRONECTIN TYPE III DOMAIN-BASED PROTEIN AND APPLICATION THEREOF

CROSS REFERENCE

The non-provisional application claims priority of Taiwan Invention Patent Application No. 111135255, filed on Sep. 16, 2022, the contents thereof are incorporated by reference herein.

STATEMENT REGARDING SEQUENCE LISTING

Reference to sequence listing is submitted electronically via EFS-web. The content of the electronically submitted sequence listing (Name: PI-111-153-US.xml, Size: 29.5 kilobytes, and Production date: Dec. 28, 2023) is incorporated herein by reference in its entirety.

FIELD OF THE INVENTION

The present invention is involved in protein engineering, and particularly directed to fibronectin type III domain-based protein and application of the same protein, including a method for treating or preventing a disease or a disorder caused by or related to vascular endothelial growth factor receptor 2 (VEGFR2) activity or signaling, or a method for treating or preventing a disease or a disorder caused by angiogenesis.

BACKGROUND OF THE INVENTION

Recent efforts to develop molecular recognition modules based-on protein scaffolds other than immunoglobulins aim to overcome the inherent limitations of immunoglobulins as molecular recognition modules, including large size, complex heterodimeric architecture, and requirement of correctly formed disulfide bonds. Its fundamental assumption is that a binding interface is constructed on a suitable protein framework or a molecular scaffold, other than an antibody to develop molecules with affinity and specificity comparable to those of antibodies.

The 10th human fibronectin type III domain (10Fn3) is one of widely used non-antibody scaffolds for engineering novel binding proteins. Many 10Fn3-based molecules are developed for therapeutic applications, and most are currently in clinical trials.

10Fn3 has several characteristics superior to immunoglobulin-based systems. 10Fn3 is a member of the immunoglobulin superfamily due to its global β-sandwich fold. The three surface loops proximal to its N-terminus are structurally equivalent to the three antigen-recognition loops or the complementarity-determining regions (CDRs) of an immunoglobulin variable domain. However, 10Fn3 lacks a disulfide bond, unlike the canonical immunoglobulin domain. 10Fn3 has a higher conformational stability, with the thermal transition above 80° C. 10Fn3 exhibits reversible and rapid unfolding and refolding. 10Fn3 has ~94 amino acid residues, less than the antigen-binding unit (VHH) of a heavy-chain antibody. All these features make 10Fn3 a particularly robust scaffold system compatible with diverse molecular display systems and with simple and efficient production methods.

U.S. patent application Ser. No. 11/448,171, entitled "INHIBITORS OF TYPE 2 VASCULAR ENDOTHELIAL GROWTH FACTOR RECEPTORS" provides a protein C7 targeting vascular endothelial growth factor receptor 2. The protein C7 is a 10Fn3-based protein and different from the wild-type form in that the sequences of the three surface loops in the wild-type form, $^{23}$DAPAVTVRY, $^{51}$PGSKST, and $^{75}$VTGRGDSPASSKP are substituted with $^{23}$RHPHFPTRY (SEQ ID NO.: 29), $^{51}$PLQPPT (SEQ ID NO.: 30), and $^{75}$VTDGRNGRLLSIP (SEQ ID NO.: 31) respectively. Since the three mutant regions are a targeting site for vascular endothelial growth factor receptor 2, the protein C7 can be used as a VEGFR2 antagonist and has the potential to be an anti-cancer drug. However, its development for becoming a drug comes to the deadlock due to the low thermostability and the low solubility.

Therefore, there is a need to develop a 10Fn3-based protein scaffold with the high thermostability and the high solubility.

SUMMARY OF THE INVENTION

A protein variant C7-NM has been obtained by modifying a protein C7. The present invention is made based on that the design of introducing a disulfide bond into a protein C7-NM is accomplished by the program Disulfide by Design 2.0 (DbD2) with reference to the parameters including a B-factor, a χ3 angle, and an energy. The newly-obtained protein variant has a high thermostability and a high solubility without effects on the activity of targeting a specific protein.

Accordingly, the present invention provides a protein, which includes a 10th human fibronectin type III domain and has a first mutation at an amino acid residue with a cysteine residue and a second mutation at another amino acid residue with another cysteine residue, wherein the first mutation and the second mutation take place at a region of the 10th human fibronectin type III domain other than a loop FG so that a disulfide bond is formed between the cysteine residue formed by the first mutation and the cysteine residue formed by the second mutation.

Exemplarily, the 10th human fibronectin type III domain comprises: an amino acid sequence of SEQ ID No.: 1.

Exemplarily, the protein further comprises: a mutation to substitute an amino acid sequence of a loop BC with RHPHFPTRY (SEQ ID NO.: 29), a mutation to substitute an amino acid sequence of a loop DE with PLQPPT (SEQ ID NO.: 30), and a mutation to substitute an amino acid sequence of a loop FG with VTDGRNGRLLSIP (SEQ ID NO.: 31).

Exemplarily, the first mutation takes place at a β-strand A, a β-strand B, a β-strand C, a β-strand D, a β-strand E, a β-strand F, a β-strand G, a loop AB, a loop BC, a loop CD, a loop DE, or a loop EF of the 10th human fibronectin type III domain, and the second mutation takes place at the β-strand A, the β-strand B, the β-strand C, the β-strand D, the β-strand E, the β-strand F, the β-strand G, the loop AB, the loop BC, the loop CD, the loop DE, or the loop EF of the 10th human fibronectin type III domain.

Exemplarily, the first mutation takes place at a β-strand A, a β-strand B, a β-strand C, a β-strand D, a β-strand E, a β-strand F, a β-strand G, a loop AB, a loop CD, or a loop EF of the 10th human fibronectin type III domain, and the second mutation takes place at the β-strand A, the β-strand B, the β-strand C, the β-strand D, the β-strand E, the β-strand F, the β-strand G, the loop AB, the loop CD, or the loop EF of the 10th human fibronectin type III domain.

Exemplarily, the first mutation and the second mutation take place at a same region or different regions.

Exemplarily, the first mutation comprises: a substitution of a leucine residue at position 8 with the cysteine residue, a substitution of a serine residue at position 17 with the cysteine residue, a substitution of a leucine residue at position 19 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue; the second mutation comprises: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue.

Exemplarily, the first mutation comprises: a substitution of a leucine residue at position 8 with the cysteine residue, and the second mutation comprises: a substitution of a tryptophan residue at position 22 with the cysteine residue; the first mutation comprises: a substitution of a leucine residue at position 8 with the cysteine residue, and the second mutation comprises: a substitution of a serine residue at position 89 with the cysteine residue; the first mutation comprises: a substitution of a serine residue at position 17 with the cysteine residue, and the second mutation comprises: a substitution of a serine residue at position 60 with the cysteine residue; the first mutation comprises: a substitution of a leucine residue at position 19 with the cysteine residue, and the second mutation comprises: a substitution of a threonine residue at position 58 with the cysteine residue; the first mutation comprises: a substitution of an isoleucine residue at position 34 with the cysteine residue, and the second mutation comprises: a substitution of a phenylalanine residue at position 48 with the cysteine residue; the first mutation comprises: a substitution of a threonine residue at position 35 with the cysteine residue, and the second mutation comprises: a substitution of a valine residue at position 45 with the cysteine residue; the first mutation comprises: a substitution of a tyrosine residue at position 36 with the cysteine residue, and the second mutation comprises: a substitution of an isoleucine residue at position 70 with the cysteine residue; the first mutation comprises: a substitution of a glycine residue at position 37 with the cysteine residue, and the second mutation comprises: a substitution of a valine residue at position 45 with the cysteine residue; the first mutation comprises: a substitution of a threonine residue at position 39 with the cysteine residue, and the second mutation comprises: a substitution of an aspartate residue at position 67 with the cysteine residue; the first mutation comprises: a substitution of a lysine residue at position 63 with the cysteine residue, and the second mutation comprises: a substitution of a valine residue at position 66 with the cysteine residue; or the first mutation comprises: a substitution of an aspartate residue at position 67 with the cysteine residue, and the second mutation comprises: a substitution of an asparagine residue at position 91 with the cysteine residue.

Exemplarily, the protein comprises: an amino acid sequence selected from SEQ ID Nos.: 4-14.

Exemplarily, the protein comprises: an amino acid sequence of SEQ ID No.: 11.

Exemplarily, the protein comprises: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue on condition that the first mutation and the second mutation do not comprise a substitution of a leucine residue at position 19 with the cysteine residue.

Exemplarily, the protein comprises: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue on condition that the first mutation comprises: a substitution of a leucine residue at position 8 with the cysteine residue, a substitution of a serine residue at position 17 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue, and the second mutation comprises: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue.

Exemplarily, the protein comprises: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue on condition that the first mutation comprises: a substitution of a leucine residue at position 8 with the cysteine residue, and the second mutation comprises: a substitution of a tryptophan residue at position 22 with the cysteine residue; the first mutation comprises: a substitution of a leucine residue at position 8 with the cysteine residue, and the second mutation comprises: a substitution of a serine residue at position 89 with the cysteine residue; the first mutation comprises: a substitution of a serine residue at position 17 with the cysteine residue, and the second mutation comprises: a substitution of a serine residue at position 60 with the cysteine residue; the first mutation comprises: a substitution of an isoleucine residue at position 34 with the cysteine residue, and the second mutation comprises: a substitution of a phenylalanine residue at position 48 with the cysteine residue; the first mutation comprises: a substitution of a threonine residue at position 35 with the cysteine residue, and the second mutation comprises: a substitution of a valine residue at position 45 with the cysteine residue; the first mutation comprises: a substitution of a tyrosine residue at position 36 with the cysteine residue, and the second mutation comprises: a substitution of an isoleucine residue at position 70 with the cysteine residue; the first mutation comprises: a substitution of a glycine residue at position 37 with the cysteine residue, and the second mutation comprises: a substitution of a valine residue at position 45 with the cysteine residue; the first mutation comprises: a substitution of a threonine residue at position 39 with the cysteine residue, and the second mutation comprises: a substitution of an aspartate residue at position 67 with the cysteine residue; the first mutation comprises: a substitution of a lysine residue at position 63 with the cysteine residue, and the second mutation comprises: a substitution of a valine residue at position 66 with the cysteine residue; or the first mutation comprises: a substitution of an aspartate residue at position 67 with the cysteine residue, and the second mutation comprises: a substitution of an asparagine residue at position 91 with the cysteine residue.

Exemplarily, the protein comprises: an amino acid sequence selected from SEQ ID Nos.: 17-26.

Exemplarily, the protein further has a third mutation at another amino acid residue with a cysteine residue and a fourth mutation at another amino acid residue with another cysteine residue, wherein the third mutation and the fourth mutation take place at a region of the 10th human fibronectin type III domain other than the loop FG so that a disulfide bond is formed between the cysteine residue formed by the third mutation and the cysteine residue formed by the fourth mutation.

Exemplarily, the third mutation takes place at the β-strand A, the β-strand B, the β-strand C, the β-strand D, the β-strand E, the β-strand F, the β-strand G, the loop AB, the loop BC, the loop CD, the loop DE, or the loop EF of the 10th human fibronectin type III domain, and the fourth mutation takes place at the β-strand A, the β-strand B, the β-strand C, the β-strand D, the β-strand E, the β-strand F, the β-strand G, the loop AB, the loop BC, the loop CD, the loop DE, or the loop EF of the 10th human fibronectin type III domain.

Exemplarily, the third mutation takes place at the β-strand A, the β-strand B, the β-strand C, the β-strand D, the β-strand E, the β-strand F, the β-strand G, the loop AB, the loop CD, or the loop EF of the 10th human fibronectin type III domain, and the fourth mutation takes place at the β-strand A, the β-strand B, the β-strand C, the β-strand D, the β-strand E, the β-strand F, the β-strand G, the loop AB, the loop CD, or the loop EF of the 10th human fibronectin type III domain.

Exemplarily, the first mutation, the second mutation, the third mutation, and the fourth mutation take place at different regions.

Exemplarily, the third mutation comprises: a substitution of a leucine residue at position 8 with the cysteine residue, a substitution of a serine residue at position 17 with the cysteine residue, a substitution of a leucine residue at position 19 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue; the fourth mutation comprises: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue.

Exemplarily, the first mutation comprises: a substitution of a leucine residue at position 8 with the cysteine residue, the second mutation comprises: a substitution of a serine residue at position 89 with the cysteine residue, the third mutation comprises: a substitution of a serine residue at position 17 with the cysteine residue, and the fourth mutation comprises: a substitution of a serine residue at position 60 with the cysteine residue; or the first mutation comprises: a substitution of a leucine residue at position 8 with the cysteine residue, the second mutation comprises: a substitution of a serine residue at position 89 with the cysteine residue, the third mutation comprises: a substitution of a threonine residue at position 39 with the cysteine residue, and the fourth mutation comprises: a substitution of an aspartate residue at position 67 with the cysteine residue.

Exemplarily, the protein comprises: an amino acid sequence of SEQ ID No.: 15 or 16.

Exemplarily, the protein comprises: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue on condition that the first mutation, the second mutation, the third mutation, and the fourth mutation do not comprise a substitution of a leucine residue at position 19 with the cysteine residue.

Exemplarily, the protein comprises: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue on condition that the first mutation comprises: a substitution of a leucine residue at position 8 with the cysteine residue, a substitution of a serine residue at position 17 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue, the second mutation comprises: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue, the third mutation comprises: a substitution of a leucine residue at position 8 with the cysteine residue, a substitution of a serine residue at position 17 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue, and the fourth mutation comprises: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue.

Exemplarily, the protein comprises: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue on condition that the first mutation comprises: a substitution of a leucine residue at position 8 with the cysteine residue, the second mutation comprises: a substitution of a serine residue at position 89 with the cysteine residue, the third mutation comprises: a substitution of a serine residue at position 17 with the cysteine residue, and the fourth mutation comprises: a substitution of a serine residue at position 60 with the cysteine residue; or the first mutation comprises: a substitution of a leucine residue at position 8 with the cysteine residue, the second mutation comprises: a substitution of a serine residue at position 89 with the cysteine residue, the third mutation comprises: a substitution of a threonine residue at position 39 with the cysteine residue, and the fourth mutation comprises: a substitution of an aspartate residue at position 67 with the cysteine residue.

Exemplarily, the protein comprises: an amino acid sequence of SEQ ID No.: 27 or 28.

Exemplarily, the protein is provided for targeting DDL4, EGFR, VEGFR2, or IGF-1R.

The protein with reference to the present invention is based on a 10th human fibronectin type III domain, and a disulfide bond is introduced at a certain position of the basal structure to increase its thermostability and solubility. In the protein with reference to the present invention, the substitution for an amino acid sequence may be further performed to construct a protein-binding interface for targeting a certain protein, e.g., DDL4, EGFR, VEGFR2, or IGF-1R. As such, the protein with reference to the present invention can be used as a receptor antagonist and has the potential to be a biopharmaceutical.

The present invention further provides a pharmaceutical composition, which includes: the foregoing protein; and a pharmaceutically acceptable carrier.

Exemplarily, the pharmaceutical composition is an orally administrable formulation, an injectable formulation, an inhalable formulation, or a topically or transdermally administrable formulation.

The present invention further provides use of the foregoing pharmaceutical composition, which is for manufacturing a medicine for treating or preventing a disease or a disorder caused by or related to vascular endothelial growth factor receptor 2 activity or signaling.

Exemplarily, the disease or the disorder caused by or related to vascular endothelial growth factor receptor 2 activity or signaling comprises: autoimmune disorder, cardiac disorder, retinopathy, renal disease, hemangioblastoma, hemangioma, thyroid hyperplasia, chronic inflammation, Meigs syndrome, pericardial effusion, pleural effusion, diabetes, endometriosis, undesirable fibrosis, or cancer.

Exemplarily, the cancer comprises: kidney cancer, pancreatic carcinoma, breast cancer, head and neck cancer, prostate cancer, malignant glioma, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

The present invention further provides a method for treating or preventing a disease or a disorder caused by or related to vascular endothelial growth factor receptor 2 activity or signaling, which includes: administering the foregoing pharmaceutical composition to a subject in need thereof to bind to the subject's vascular endothelial growth factor receptor 2 so as to inhibit an activity thereof.

Exemplarily, the disease or the disorder caused by or related to vascular endothelial growth factor receptor 2 activity or signaling comprises: autoimmune disorder, cardiac disorder, retinopathy, renal disease, hemangioblastoma, hemangioma, thyroid hyperplasia, chronic inflammation, Meigs syndrome, pericardial effusion, pleural effusion, diabetes, endometriosis, undesirable fibrosis, or cancer.

Exemplarily, the cancer comprises: kidney cancer, pancreatic carcinoma, breast cancer, head and neck cancer, prostate cancer, malignant glioma, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

The present invention further provides use of the foregoing pharmaceutical composition, which is for manufacturing a medicine for treating or preventing a disease or a disorder caused by angiogenesis.

Exemplarily, the disease or the disorder caused by angiogenesis comprises: autoimmune disorder, cardiac disorder, retinopathy, renal disease, hemangioblastoma, hemangioma, thyroid hyperplasia, chronic inflammation, Meigs syndrome, pericardial effusion, pleural effusion, diabetes, endometriosis, undesirable fibrosis, or cancer.

Exemplarily, the cancer comprises: kidney cancer, pancreatic carcinoma, breast cancer, head and neck cancer, prostate cancer, malignant glioma, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

The present invention further provides a method for treating or preventing a disease or a disorder caused by angiogenesis, which includes: administering the foregoing pharmaceutical composition to a subject in need thereof to bind to the subject's vascular endothelial growth factor receptor 2 so as to inhibit angiogenesis.

Exemplarily, the disease or the disorder caused by angiogenesis comprises: autoimmune disorder, cardiac disorder, retinopathy, renal disease, hemangioblastoma, hemangioma, thyroid hyperplasia, chronic inflammation, Meigs syndrome, pericardial effusion, pleural effusion, diabetes, endometriosis, undesirable fibrosis, or cancer.

Exemplarily, the cancer comprises: kidney cancer, pancreatic carcinoma, breast cancer, head and neck cancer, prostate cancer, malignant glioma, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

The present invention further provides a nucleic acid, which includes a nucleotide sequence for encoding the foregoing protein.

The present invention further provides a host cell, which has the foregoing nucleic acid.

Exemplarily, the host cell is a prokaryotic cell or a eukaryotic cell.

Exemplarily, the prokaryotic cell is *Escherichia coli*; the eukaryotic cell is a CHO cell, a COS cell, or a HEK293 cell.

The present invention further provides a method for producing the foregoing protein, which includes: incubating the foregoing host cell to express the protein.

DETAILED DESCRIPTION OF THE INVENTION

Figure 1:
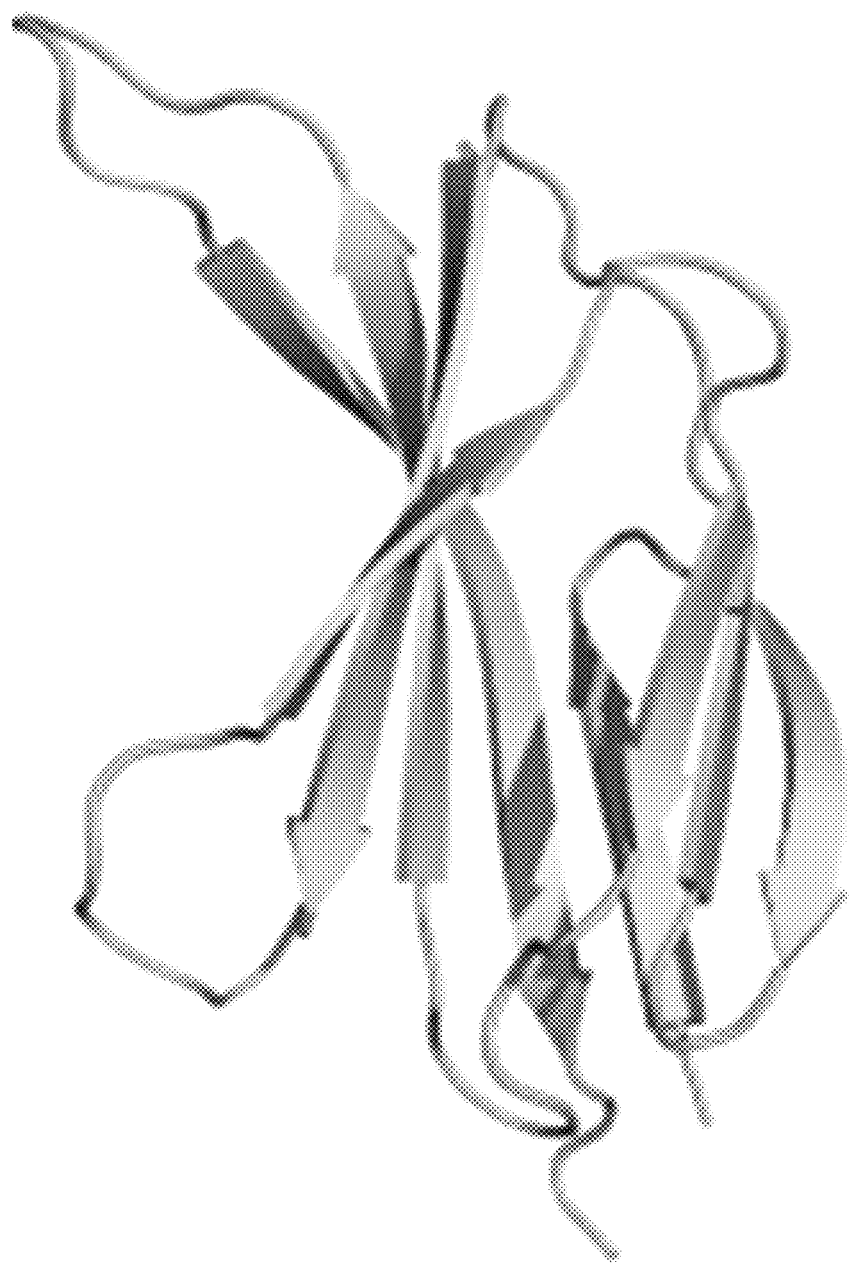
FIG. 1 is a protein structure diagram showing the 3-dimensional structure of protein C7-NM.

The detailed description and preferred embodiments of the invention will be set forth in the following content, and provided for people skilled in the art to understand the characteristics of the invention.

1. Definitions

The term "protein" used herein includes a wild-type protein produced by a natural cell, a recombinant protein made through genetic engineering, or a synthetic protein made through chemical synthesis, unless otherwise provided. Upon the condition of no adverse effect on the original activity, substitution, deletion, and/or insertion of at least one amino acid may be included in the protein sequence.

The term "amino acid" used herein includes: D-amino acid or L-amino acid, unless otherwise provided. "D-" and "L-" are used to refer to the absolute configuration of amino acid, rather than a particular rotation direction of plane-polarized light. In the present disclosure, amino acid may be referred to by the one-letter symbol recommended by the IUPAC-IUB Biochemical Nomenclature Commission, unless otherwise provided. A character string composed of multiple one-letter symbols is used to represent a protein sequence, and the order of one-letter symbol in the protein sequence corresponds to the direction from the N-terminus to the C-terminus of amino acid in the protein. If there is a superscript deposited in front of a one-letter symbol, it indicates the number of the corresponding amino acid residue from the N-terminus. For example, $^{23}$DAPAVTVRY indicate that aspartate is at position 23 from the N-terminus of a protein, and so on.

Substitution, deletion, and/or insertion in a protein sequence may occur in the protein non-functional domain, which usually has no effect on the original activity. Additionally, amino acid substitution may include conservative amino acid substitution, and conservative amino acid substitution indicates substitution within amino acid residues having a similar characteristic or within amino acid residues having a related side-chain. Substitution within amino acid residues having a similar characteristic, for example, is substitution within acidic amino acid residues, i.e., aspartate and glutamate, substitution within basic amino acid residues, i.e., lysine, arginine, and histidine, substitution within non-polar amino acid residues, i.e., alanine, valine, leucine, isoleucine, proline, phenylalanine, methionine, and tryptophan, or substitution within uncharged amino acid residues, i.e., glycine, asparagine, glutamine, cysteine, serine, threonine, and tyrosine. Substitution within amino acid residues having a related side-chain, for example, is substitution within aliphatic-hydroxy amino acid residues, i.e., serine and threonine, substitution within amide-containing amino acid residues, i.e., asparagine and glutamine, substitution within aliphatic amino acid residues, i.e., alanine, valine, leucine, and isoleucine, or substitution within aromatic amino acid residues, i.e., phenylalanine, tryptophan, and tyrosine.

The term "10th human fibronectin type III domain" used herein includes a N-terminal region, a β-strand A, a loop AB, a β-strand B, a loop BC, a β-strand C, a loop CD, a β-strand D, a loop DE, a β-strand E, a loop EF, a β-strand F, a loop FG, a β-strand G, and a C-terminal region from the N-terminus to the C-terminus, and contains at least 94 amino acid residues without any disulfide bond, unless otherwise provided, e.g., SEQ ID No.: 1. With reference to U.S. patent application Ser. No. 13/757,664, entitled "FIBRONECTIN BINDING DOMAINS WITH REDUCED IMMUNOGENICITY", the N-terminal region is defined as the protein fragment at positions 1-7, the β-strand A is defined as the protein fragment at positions 8-13, the loop AB is defined as the protein fragment at positions 14-17, the β-strand B is defined as the protein fragment of positions 18-22, the loop BC is defined as the protein fragment at positions 23-31, the β-strand C is defined as the protein fragment at positions 32-36, the loop CD is defined as the protein fragment at positions 37-47, the β-strand D is defined as the protein fragment at positions 48-50, the loop DE is defined as the protein fragment at positions 51-56, the β-strand E is defined as the protein fragment at positions 57-62, the loop EF is defined as the protein fragment at positions 63-67, the β-strand F is defined as the protein fragment at positions 68-74, the loop FG is defined as the protein fragment at positions 75-87, the β-strand G is defined as the protein fragment at positions 88-92, and the C-terminal region is defined as the protein fragment at positions 93 and 94. The loop BC, the loop DE, and the loop FG are formed at a side of the molecule, and the loop AB, the loop CD, and the loop EF are formed at another side of the molecule. For example, the N-terminal region includes $^1$VSDVPRD, the β-strand A includes $^8$LEVVAA, the loop AB includes $^{14}$TPTS, the β-strand B includes $^{18}$LLISW, the loop BC includes $^{23}$DAPAVTVRY, the β-strand C includes $^{32}$YRITY, the loop CD includes $^{37}$GETGGNSPVQE, the β-strand D includes $^{48}$FTV, the loop DE includes $^{51}$PGSKST, the β-strand E includes $^{57}$ATISGL, the loop EF includes $^{63}$KPGVD, the β-strand F includes $^{68}$YTITVYA, the loop FG includes $^{75}$VTGRGDSPASSKP, the β-strand G includes $^{88}$ISINY, and the C-terminal regions includes $^{93}$RT.

The term "protein C7" used herein is intended to refer to a variant of the 10th human fibronectin type III domain, which can bind to vascular endothelial growth factor receptor 2 to inhibit the activity thereof, unless otherwise provided, e.g., SEQ ID No.: 2. Specifically, its protein sequence relative to the wild-type loop BC comprises $^{23}$RHPHFPTRY (SEQ ID NO.: 29), its protein sequence relative to the wild-type loop DE comprises $^{51}$PLQPPT (SEQ ID NO.: 30), and its protein sequence relative to the wild-type loop FG comprises $^{75}$VTDGRNGRLLSIP (SEQ ID NO.: 31). The three mutant regions together form a target interface to vascular endothelial growth factor receptor 2.

The term "protein C7-NM" used herein refers to a variant of protein C7, unless otherwise provided, e.g., SEQ ID No.: 3. Specifically, its amino acid relative that of the reference protein at position 12 is glutamate, its amino acid relative that of the reference protein at position 14 is serine, its amino acid relative that of the reference protein at position 18 is isoleucine, and its amino acid relative that of the reference protein at position 19 is glutamine.

The term "vascular endothelial growth factor receptor 2" used herein refers to a transmembrane receptor tyrosine kinase, which can regulate the angiogenesis caused by VEGF-A and VEGF-B, unless otherwise provided. The term "vascular endothelial growth factor receptor 2" is synonymous with the term "kinase insert domain receptor (KDR)" and the term "fetal liver kinase 1 (FLK-1)", and all are exchangeable.

The term "treating" used herein indicates to provide a therapeutic intervention for curing or ameliorating disease or disorder, unless otherwise provided. That is, treating comprises completely or almost completely curing or ameliorating the disease or disorder.

The term "preventing" used herein indicates to completely or almost completely stop disease or disorder from occurring, unless otherwise provided. For example, when a subject has no disease or disorder or is suspected to have disease or disorder but not resulting in the disease or disorder, a preventive intervention is provided to prevent the disease or disorder from occurring.

The term "pharmaceutically acceptable carrier" used herein indicates an additive which is, within the scope of sound medical judgment, suitable for use in contact with the tissue of a subject without excessive toxicity, irritation, allergic response, or other problem or complication, and commensurate with a reasonable benefit/risk ratio, unless otherwise provided, e.g., a filler, a dilutant, an agglutinant, an adhesive, a lubricant, a fluidizer, a stabilizer, a colorant, a humectant, or a disintegrant.

2. 10th Human Fibronectin Type III Domain-Based Protein

A first embodiment of the present invention discloses a protein, which is based on the 10th human fibronectin type III domain and has a disulfide bond introduced at a certain site of the basal structure. In such a way, the thermostability and solubility of protein increase. With the foregoing high thermostability and high solubility and the properties originally exhibited in the 10th human fibronectin type III domain, amino acid substitution can be performed to construct a protein-binding interface for targeting a certain protein, e.g., DDL4, EGFR, VEGFR2, or IGF-1R. Accordingly, the protein of the present embodiment can be used as an antagonist and has the potential to be a biopharmaceutical.

The protein of the present embodiment includes a 10th human fibronectin type III domain and has a first mutation at an amino acid residue with a cysteine residue and a second mutation at another amino acid residue with another cysteine residue, wherein the first mutation and the second mutation take place at a region of the 10th human fibronectin type III domain other than a loop FG so that a disulfide bond is formed between the cysteine residue formed by the first mutation and the cysteine residue formed by the second mutation. Preferably, the 10th human fibronectin type III domain comprises SEQ ID No.: 1.

In term of the region, the first mutation may take place at a β-strand A, a β-strand B, a β-strand C, a β-strand D, a β-strand E, a β-strand F, a β-strand G, a loop AB, a loop BC, a loop CD, a loop DE, or a loop EF of the 10th human fibronectin type III domain; the second mutation may take place at the β-strand A, the β-strand B, the β-strand C, the β-strand D, the β-strand E, the β-strand F, the β-strand G, the loop AB, the loop BC, the loop CD, the loop DE, or the loop EF of the 10th human fibronectin type III domain. Preferably, the first mutation takes place at the β-strand A, the β-strand B, the β-strand C, the β-strand D, the β-strand E, the β-strand F, the β-strand G, the loop AB, the loop CD, or the loop EF of the 10th human fibronectin type III domain; the second mutation takes place at the β-strand A, the β-strand B, the β-strand C, the β-strand D, the β-strand E, the β-strand F, the β-strand G, the loop AB, the loop CD, or the loop EF of the 10th human fibronectin type III domain.

The first mutation and the second mutation may take place at a same region of the foregoing region group or two different regions of the foregoing region group. For example, both the first mutation and the second mutation take place at the loop CD; or both the first mutation and the second mutation take place at the loop EF. For example, the first mutation takes place at the β-strand A, and the second mutation takes place at the β-strand B; the first mutation takes place at the β-strand A, and the second mutation takes place at the β-strand G; the first mutation takes place at the loop AB, and the second mutation takes place at the β-strand E; the first mutation takes place at the β-strand B, and the second mutation takes place at the β-strand E; the first mutation takes place at the β-strand C, and the second mutation takes place at the β-strand D; the first mutation takes place at the β-strand C, and the second mutation takes place at the loop CD; the first mutation takes place at the β-strand C, and the second mutation takes place at the β-strand F; the first mutation takes place at the loop CD, and the second mutation takes place at the loop EF; or the first mutation takes place at the loop EF, and the second mutation takes place at the β-strand G.

In term of the protein sequence, the first mutation may comprise: a substitution of a leucine residue at position 8 with the cysteine residue, a substitution of a serine residue at position 17 with the cysteine residue, a substitution of a leucine residue at position 19 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue; the second mutation may comprise: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue. Specifically, the first mutation may comprise: a substitution of a leucine residue at position 8 with the cysteine residue, and the second mutation may comprise: a substitution of a tryptophan residue at position 22 with the cysteine residue; the first mutation may comprise: a substitution of a leucine residue at position 8 with the cysteine residue, and the second mutation may comprise: a substitution of a serine residue at position 89 with the cysteine residue; the first mutation may comprise: a substitution of a serine residue at position 17 with the cysteine residue, and the second mutation may comprise: a substitution of a serine residue at position 60 with the cysteine residue; the first mutation may comprise: a substitution of a leucine residue at position 19 with the cysteine residue, and the second mutation may comprise: a substitution of a threonine residue at position 58 with the cysteine residue; the first mutation may comprise: a substitution of an isoleucine residue at position 34 with the cysteine residue, and the second mutation may comprise: a substitution of a phenylalanine residue at position 48 with the cysteine residue; the first mutation may comprise: a substitution of a threonine residue at position 35 with the cysteine residue, and the second mutation may comprise: a substitution of a valine residue at position 45 with the cysteine residue; the first mutation may comprise: a substitution of a tyrosine residue at position 36 with the cysteine residue, and the second mutation may comprise: a substitution of an isoleucine residue at position 70 with the cysteine residue; the first mutation may comprise: a substitution of a glycine residue at position 37 with the cysteine residue, and the second mutation may comprise: a substitution of a valine residue at position 45 with the cysteine residue; the first mutation may comprise: a substitution of a threonine residue at position 39 with the cysteine residue, and the second mutation may comprise: a substitution of an aspartate residue at position 67 with the cysteine residue; the first mutation may comprise: a substitution of a lysine residue at position 63 with the cysteine residue, and the second mutation may comprise: a substitution of a valine residue at position 66 with the cysteine residue; or the first mutation may comprise: a substitution of an aspartate residue at position 67 with the cysteine residue, and the second mutation may comprise: a substitution of an asparagine residue at position 91 with the cysteine residue.

The protein may further have a third mutation at another amino acid residue with a cysteine residue and a fourth mutation at another amino acid residue with another cysteine residue, wherein the third mutation and the fourth mutation take place at a region of the 10th human fibronectin type III domain other than the loop FG so that a disulfide bond is formed between the cysteine residue formed by the third mutation and the cysteine residue formed by the fourth mutation. On condition of having the at least two disulfide bonds, the thermostability and the solubility of the protein can enhance.

In term of the region, the third mutation may take place at the β-strand A, the β-strand B, the β-strand C, the β-strand D, the β-strand E, the β-strand F, the β-strand G, the loop AB, the loop BC, the loop CD, the loop DE, or the loop EF of the 10th human fibronectin type III domain, and the fourth mutation may take place at the β-strand A, the β-strand B, the β-strand C, the β-strand D, the β-strand E, the β-strand F, the β-strand G, the loop AB, the loop BC, the loop CD, the loop DE, or the loop EF of the 10th human fibronectin type III domain. Preferably, the third mutation takes place at the β-strand A, the β-strand B, the β-strand C, the β-strand D, the β-strand E, the β-strand F, the β-strand G, the loop AB, the loop CD, or the loop EF of the 10th human fibronectin type III domain, and the fourth mutation takes place at the β-strand A, the β-strand B, the β-strand C, the β-strand D, the β-strand E, the β-strand F, the β-strand G, the loop AB, the loop CD, or the loop EF of the 10th human fibronectin type III domain.

The first mutation, the second mutation, the third mutation, and the fourth mutation may take place at four different regions of the foregoing region group. For example, the first mutation takes place at the β-strand A, the second mutation takes place at the β-strand G, the third mutation takes place at the loop AB, and the fourth mutation takes place at the β-strand E; or the first mutation takes place at the β-strand A, the second mutation takes place at the β-strand G, the third mutation takes place at the loop CD, and the fourth mutation takes place at the loop EF.

In term of the protein sequence, the third mutation may comprise: a substitution of a leucine residue at position 8 with the cysteine residue, a substitution of a serine residue at position 17 with the cysteine residue, a substitution of a leucine residue at position 19 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue; the fourth mutation may comprise: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue. Specifically, the first mutation may comprise: a substitution of a leucine residue at position 8 with the cysteine residue, the second mutation may comprise: a substitution of a serine residue at position 89 with the cysteine residue, the third mutation may comprise: a substitution of a serine residue at position 17 with the cysteine residue, and the fourth mutation may comprise: a substitution of a serine residue at position 60 with the cysteine residue; or the first mutation may comprise: a substitution of a leucine residue at position 8 with the cysteine residue, the second mutation may comprise: a substitution of a serine residue at position 89 with the cysteine residue, the third mutation may comprise: a substitution of a threonine residue at position 39 with the cysteine residue, and the fourth mutation may comprise: a substitution of an aspartate residue at position 67 with the cysteine residue.

As described above, the protein of the present embodiment can target DDL4, EGFR, VEGFR2, or IGF-1R. For targeting VEGFR2, the protein of the present embodiment may further comprise: a mutation to substitute an amino acid sequence of the loop BC with RHPHFPTRY (SEQ ID NO.: 29), a mutation to substitute an amino acid sequence of the loop DE with PLQPPT (SEQ ID NO.: 30), and a mutation to substitute an amino acid sequence of the loop FG with VTDGRNGRLLSIP (SEQ ID NO.: 31).

Preferably, the protein of the present embodiment comprises: an amino acid sequence of SEQ ID No.: 4, 5, 6, 7, 8, 9, 10, 11, 12, 13, 14, 15, or 16. More preferably, the protein of the present embodiment comprises: an amino acid sequence of SEQ ID No.: 11, 15, or 16.

According to the previous discovery, protein C7-NM could increase the thermostability and the solubility. The protein of the present embodiment may be modified with reference to the protein sequence of protein C7-NM.

On condition that the first mutation and the second mutation do not comprise a substitution of the leucine residue at position 19 with the cysteine residue, the protein of the present embodiment may further comprise: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue. Specifically, on condition that the first mutation comprises: a substitution of a leucine residue at position 8 with the cysteine residue, a substitution of a serine residue at position 17 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue, and the second mutation comprises: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue, the protein of the present embodiment may further comprise: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue. More specifically, on condition that the first mutation comprises: a substitution of a leucine residue at position 8 with the cysteine residue, and the second mutation comprises: a substitution of a tryptophan residue at position 22 with the cysteine residue; the first mutation comprises: a substitution of a leucine residue at position 8 with the cysteine residue, and the second mutation comprises: a substitution of a serine residue at position 89 with the cysteine residue; the first mutation comprises: a substitution of a serine residue at position 17 with the cysteine residue, and the second mutation comprises: a substitution of a serine residue at position 60 with the cysteine residue; the first mutation comprises: a substitution of an isoleucine residue at position 34 with the cysteine residue, and the second mutation comprises: a substitution of a phenylalanine residue at position 48 with the cysteine residue; the first mutation comprises: a substitution of a threonine residue at position 35 with the cysteine residue, and the second mutation comprises: a substitution of a valine residue at position 45 with the cysteine residue; the first mutation comprises: a substitution of a tyrosine residue at position 36 with the cysteine residue, and the second mutation comprises: a substitution of an isoleucine residue at position 70 with the cysteine residue; the first mutation comprises: a substitution of a glycine residue at position 37 with the cysteine residue, and the second mutation comprises: a substitution of a valine residue at position 45 with the cysteine residue; the first mutation comprises: a substitution of a threonine residue at position 39 with the cysteine residue, and the second mutation comprises: a substitution of an aspartate residue at position 67 with the cysteine residue; the first mutation comprises: a substitution of a lysine residue at position 63 with the cysteine residue, and the second mutation comprises: a substitution of a valine residue at position 66 with the cysteine residue; or the first mutation comprises: a substitution of an aspartate residue at position 67 with the cysteine residue, and the second mutation comprises: a substitution of an asparagine residue at position 91 with the cysteine residue, the protein of the present embodiment may further comprise: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue.

Preferably, the protein of the present embodiment comprises: an amino acid sequence of SEQ ID No.: 17, 18, 19, 20, 21, 22, 23, 24, 25, or 26.

On condition that the first mutation, the second mutation, the third mutation, and the fourth mutation do not comprise a substitution of a leucine residue at position 19 with the cysteine residue, the protein of the present embodiment may further comprise: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue. Specifically, on condition that the first mutation comprises: a substitution of a leucine residue at position 8 with the cysteine residue, a substitution of a serine residue at position 17 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue, the second mutation comprises: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue, the third mutation comprises: a substitution of a leucine residue at position 8 with the cysteine residue, a substitution of a serine residue at position 17 with the cysteine residue, a substitution of an isoleucine residue at position 34 with the cysteine residue, a substitution of a threonine residue at position 35 with the cysteine residue, a substitution of a tyrosine residue at position 36 with the cysteine residue, a substitution of a glycine residue at position 37 with the cysteine residue, a substitution of a threonine residue at position 39 with the cysteine residue, a substitution of a lysine residue at position 63 with the cysteine residue, or a substitution of an aspartate residue at position 67 with the cysteine residue, and the fourth mutation comprises: a substitution of a tryptophan residue at position 22 with the cysteine residue, a substitution of a valine residue at position 45 with the cysteine residue, a substitution of a phenylalanine residue at position 48 with the cysteine residue, a substitution of a threonine residue at position 58 with the cysteine residue, a substitution of a serine residue at position 60 with the cysteine residue, a substitution of a valine residue at position 66 with the cysteine residue, a substitution of an aspartate residue at position 67 with the cysteine residue, a substitution of an isoleucine residue at position 70 with the cysteine residue, a substitution of a serine residue at position 89 with the cysteine residue, or a substitution of an asparagine residue at position 91 with the cysteine residue, the protein of the present embodiment may further comprise: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue. More specifically, on condition that the first mutation comprises: a substitution of a leucine residue at position 8 with the cysteine residue, the second mutation comprises: a substitution of a serine residue at position 89 with the cysteine residue, the third mutation comprises: a substitution of a serine residue at position 17 with the cysteine residue, and the fourth mutation comprises: a substitution of a serine residue at position 60 with the cysteine residue; or the first mutation comprises: a substitution of a leucine residue at position 8 with the cysteine residue, the second mutation comprises: a substitution of a serine residue at position 89 with the cysteine residue, the third mutation comprises: a substitution of a threonine residue at position 39 with the cysteine residue, and the fourth mutation comprises: a substitution of an aspartate residue at position 67 with the cysteine residue, the protein of the present embodiment may further comprise: a mutation to substitute an alanine residue at position 12 with a glutamate residue, a mutation to substitute a threonine residue at position 14 with a serine residue, a mutation to substitute a leucine residue at position 18 with an isoleucine residue, and a mutation to substitute a leucine residue at position 19 with a glutamine residue.

Preferably, the protein of the present embodiment comprises: an amino acid sequence of SEQ ID No.: 27 or 28.

The protein of the present embodiment may be produced through genetic engineering or chemical synthesis. The chemical synthesis, for example, is solid-phase synthesis or liquid-phase synthesis. Ammonium sulfate or ethanol precipitation, acid extraction, ion-exchange chromatography, affinity chromatography, or lectin chromatography may be implemented for isolation and purification of the protein of the present embodiment. Preferably, high performance liquid chromatography (HPLC) is implemented.

The protein of the present embodiment may further include a hydrophilic group for increasing its solubility or circulation half-life. The hydrophilic group may be connected to a N-terminus of the protein. Preferably, the hydrophilic group is polyethylene glycol, polypropylene glycol, polylactic acid, polyglycolic acid, polyvinyl alcohol, or dextran. More preferably, the hydrophilic group is polyethylene glycol containing 2-40 repeating ethylene glycol units.

The protein of the present embodiment may further include an affinity tag for protein purification. The affinity tag may be connected to a N-terminus or a C-terminus of the protein. Preferably, the affinity tag is a His-tag, a GST-tag, a MBP-tag, a NusA-tag, or a SUMO-tag.

3. Pharmaceutical Composition

A second embodiment of the present invention discloses a pharmaceutical composition including the protein of the first embodiment. The pharmaceutical composition can be administered to a subject to bind to a certain protein therein so that the pharmaceutical composition can be used as an antagonist against the certain protein and inhibit the activity or the signaling thereof. The pharmaceutical composition of the second embodiment comprises: the protein of the first embodiment; and a pharmaceutically acceptable carrier.

Generally, the pharmaceutically acceptable carrier can allow the pharmaceutical composition to be in various forms or to be suitable in various routes of administration. Preferably, the pharmaceutical composition is an orally administrable formulation, an injectable formulation, an inhalable formulation, or a topically or transdermally administrable formulation for various routes of administration. Preferably, the pharmaceutical composition is a tablet, a capsule, a granule, a dispersant, a solution, a syrup, a suspension, or an emulsion.

The pharmaceutically acceptable carrier may be an excipient, a filler, a dilutant, an agglutinant, an adhesive, a lubricant, a fluidizer, a stabilizer, a colorant, a humectant, or a disintegrant. The excipient, for example, is sodium citrate, calcium carbonate, or calcium phosphate; the filler, for example, is lactose or high molecular weight polyethylene glycol; the dilutant, for example, is water, ethanol, propanediol, or glycerol; the adhesive, for example, is sucrose, gelatin, or acacia gum; the lubricant, for example, is magnesium stearate, calcium stearate, zinc stearate, sodium stearate, stearate, aluminum stearate, leucine, glycerol behenate, or hydrogenated vegetable oil; the fluidizer, for example, is sodium aluminosilicate, calcium silicate, microcrystalline cellulose, maize starch, sodium benzoate, calcium carbonate, magnesium carbonate, talcum, calcium stearate, magnesium stearate, zinc stearate, magnesium lauryl sulfate, or magnesium oxide; the stabilizer, for example, is citrate or ascorbic acid; the colorant, for example, is titanium dioxide or ferric oxide; the humectant, for example, is Pluronic F68, Tween 20, or Tween 80; the disintegrant, for example, is potato starch, tapioca starch, or silicate.

4. Pharmaceutical Use

A third embodiment of the present invention discloses use of a pharmaceutical composition of the second embodiment, which is for manufacturing a medicine for treating or preventing a disease or a disorder caused by or related to vascular endothelial growth factor receptor 2 activity or signaling. This medicine can be administered to a subject to inhibit vascular endothelial growth factor receptor 2 activity or signaling. That is, this medicine can be administered to a subject in need of treating or preventing a disease or a disorder caused by or related to vascular endothelial growth factor receptor 2 activity or signaling so that the treatment or prevention effect can be achieved by inhibiting vascular endothelial growth factor receptor 2 activity or signaling in the subject.

This medicine may be administered by different routes, e.g., oral administration, injection administration, inhalation administration, or topical or transdermal administration.

The disease or the disorder caused by or related to vascular endothelial growth factor receptor 2 activity or signaling may comprise: autoimmune disorder, cardiac disorder, retinopathy, renal disease, hemangioblastoma, hemangioma, thyroid hyperplasia, chronic inflammation, Meigs syndrome, pericardial effusion, pleural effusion, diabetes, endometriosis, undesirable fibrosis, or cancer. Preferably, the cancer comprises: kidney cancer, pancreatic carcinoma, breast cancer, head and neck cancer, prostate cancer, malignant glioma, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

A fourth embodiment of the present invention discloses a method for treating or preventing a disease or a disorder caused by or related to vascular endothelial growth factor receptor 2 activity or signaling, which includes: administering the pharmaceutical composition of the second embodiment to a subject in need thereof to bind to the subject's vascular endothelial growth factor receptor 2 so as to inhibit the activity or block the signaling.

This pharmaceutical composition may be administered by different routes, e.g., oral administration, injection administration, inhalation administration, or topical or transdermal administration.

The disease or the disorder caused by or related to vascular endothelial growth factor receptor 2 activity or signaling may comprise: autoimmune disorder, cardiac disorder, retinopathy, renal disease, hemangioblastoma, hemangioma, thyroid hyperplasia, chronic inflammation, Meigs syndrome, pericardial effusion, pleural effusion, diabetes, endometriosis, undesirable fibrosis, or cancer. Preferably, the cancer comprises: kidney cancer, pancreatic carcinoma, breast cancer, head and neck cancer, prostate cancer, malignant glioma, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

A fifth embodiment of the present invention discloses use of the pharmaceutical composition of the second embodiment, which is for manufacturing a medicine for treating or preventing a disease or a disorder caused by angiogenesis. This medicine can be administered to a subject to inhibit angiogenesis. That is, this medicine can be administered to a subject in need of treating or preventing a disease or a disorder caused by angiogenesis so that the treatment or prevention effect can be achieved by inhibiting angiogenesis in the subject.

This medicine may be administered by different routes, e.g., oral administration, injection administration, inhalation administration, or topical or transdermal administration.

The disease or the disorder caused by angiogenesis may comprise: autoimmune disorder, cardiac disorder, retinopathy, renal disease, hemangioblastoma, hemangioma, thyroid hyperplasia, chronic inflammation, Meigs syndrome, pericardial effusion, pleural effusion, diabetes, endometriosis, undesirable fibrosis, or cancer. Preferably, the cancer comprises: kidney cancer, pancreatic carcinoma, breast cancer, head and neck cancer, prostate cancer, malignant glioma, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

A sixth embodiment of the present invention discloses a method for treating or preventing a disease or a disorder caused by angiogenesis, which includes: administering the pharmaceutical composition of the second embodiment to a subject in need thereof to bind to the subject's vascular endothelial growth factor receptor 2 so as to inhibit angiogenesis.

This pharmaceutical composition may be administered by different routes, e.g., oral administration, injection administration, inhalation administration, or topical or transdermal administration.

The disease or the disorder caused by angiogenesis may comprise: autoimmune disorder, cardiac disorder, retinopathy, renal disease, hemangioblastoma, hemangioma, thyroid hyperplasia, chronic inflammation, Meigs syndrome, pericardial effusion, pleural effusion, diabetes, endometriosis, undesirable fibrosis, or cancer. Preferably, the cancer comprises: kidney cancer, pancreatic carcinoma, breast cancer, head and neck cancer, prostate cancer, malignant glioma, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma.

5. Others

A seventh embodiment of the present invention discloses a nucleic acid, which includes a nucleotide sequence for encoding the protein of the first embodiment. For controlling the protein expression, the nucleic acid may further include a promoter, which is operably linked to the nucleotide sequence for encoding the protein. The term "being operably linked to" herein indicates that two or more than two nucleotide sequences are in a functional relationship with each other.

An eighth embodiment of the present invention discloses a host cell, which includes the nucleic acid of the seventh embodiment. Since the host cell has the nucleotide sequence for encoding the protein, the protein can be produced through cultivating the host cell. The host cell may be a prokaryotic cell or a eukaryotic cell. The prokaryotic cell, for example, is *Escherichia coli*; the eukaryotic cell, for example, is a CHO cell, a COS cell, or a HEK293 cell.

A ninth embodiment of the present invention discloses a method for producing the protein of the first embodiment, which includes: incubating the host cell of the eighth embodiment to express the protein. Further, an inducer may be selected for inducing the host cell to express the protein according to the promoter.

The following examples are offered to further illustrate the invention.

Example 1: Design of Introducing Disulfide Bond

Figure 2:
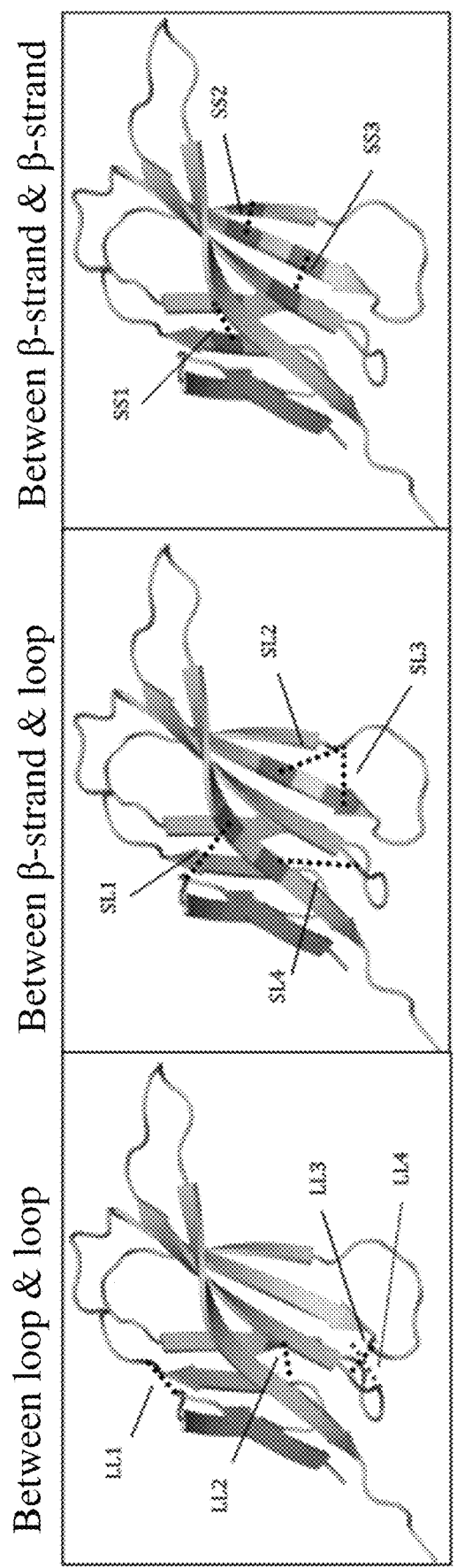
FIG. 2 is a protein structure diagram showing designable sites for disulfide bond formation in protein C7-NM.

As shown in FIG. 1, protein C7-NM has 8 β-strands and a loop is formed between two adjacent β-strands. Protein C7-NM was used as parent protein, and the program Disulfide by Design 2.0 (DbD2) was used for design of introducing a disulfide bond into the parent protein with reference to the parameters including a B-factor, a $\chi 3$ angle, and an energy. As shown in FIG. 2 and Table 1, the designable site for disulfide bond formation is between two β-strands, between two loops, or between one β-strand and one loop. The amino acid sequences of variant proteins having at least one disulfide bond are listed in Table 2, and each variant protein is obtained by introducing the amino acid sequence of protein C7 as reference sequence and performing amino acid substitution thereon according to the designable site for disulfide bond formation.

TABLE 1

| | crystallography parameter | | | |
|---|---|---|---|---|
| | Site for disulfide bond formation | $\chi 3$ angle | Energy | B-factor |
| C7-LL1 | $L9^{loop}/W23^{loop}$ | +108.9 | 0.96 | 32.53 |
| C7-LL2 | $S18^{loop}/S61^{loop}$ | +118.6 | 2.83 | 30.52 |
| C7-LL3 | $T40^{loop}/D68^{loop}$ | −78.0 | 1.46 | 54.97 |
| C7-LL4 | $K64^{loop}/V67^{loop}$ | +81.4 | 2.43 | 33.68 |
| C7-SS1 | $L20^{strand}/T59^{strand}$ | +122.0 | 2.56 | 33.88 |
| C7-SS2 | $I35^{strand}/F49^{strand}$ | | | |
| C7-SS3 | $Y37^{strand}/I71^{strand}$ | +125.7 | 3.11 | 27.37 |
| C7-SL1 | $L9^{loop}/S90^{strand}$ | +95.7 | 5.48 | 29.88 |
| C7-SL2 | $T36^{strand}/V46^{loop}$ | +120.0 | 3.61 | 48.37 |
| C7-SL3 | $G38^{strand}/V46^{loop}$ | −86.9 | 4.52 | 49.88 |
| C7-SL4 | $D68^{loop}/N92^{strand}$ | | | |

TABLE 2

| Protein | Sequence |
|---|---|
| 10Fn3-WT | VSDVPRDLEVVAATPTSLLISWDAPAVTVRYYRITYGETGGNSPVQEFTVPGSKSTATISG LKPGVDYTITVYAVTGRGDSPASSKPISINYRT |
| C7 | VSDVPRDLEVVAATPTSLLISW[RH]P[HFPT]RYYRITYGETGGNSPVQEFTVP[LQPP]TATISG LKPGVDYTITVYAVT[DGRNGRLL]S[I]PISINYRT |
| C7-NM | MVSDVPRDLEVVEASPTSIQISW[RH]P[HFPT]RYYRITYGETGGNSPVQEFTVP[LQPP]TATIS GLKPGVDYTITVYAVT[DGRNGRLL]S[I]PISINYRTHHHHHH |
| C7-LL1-His | MVSDVPRDCEVVAATPTSLLISC[RH]P[HFPT]RYYRITYGETGGNSPVQEFTVP[LQPP]TATIS GLKPGVDYTITVYAVT[DGRNGRLL]S[I]PISINYRTHHHHHH |
| C7-LL2-His | MVSDVPRDLEVVAATPTCLLISW[RH]P[HFPT]RYYRITYGETGGNSPVQEFTVP[LQPP]TATI CGLKPGVDYTITVYAVT[DGRNGRLL]S[I]PISINYRTHHHHHH |
| C7-LL3-His | MVSDVPRDLEVVAATPTSLLISW[RH]P[HFPT]RYYRITYGECGGNSPVQEFTVP[LQPP]TATI SGLKPGVCYTITVYAVT[DGRNGRLL]S[I]PISINYRTHHHHHH |
| C7-LL4-His | MVSDVPRDLEVVAATPTSLLISW[RH]P[HFPT]RYYRITYGETGGNSPVQEFTVP[LQPP]TATI SGLCPGCDYTITVYAVT[DGRNGRLL]S[I]PISINYRTHHHHHH |
| C7-SS1-His | MVSDVPRDLEVVAATPTSLCISW[RH]P[HFPT]RYYRITYGETGGNSPVQEFTVP[LQPP]TACI SGLKPGVDYTITVYAVT[DGRNGRLL]S[I]PISINYRTHHHHHH |

TABLE 2-continued amino acid sequence

| Protein | Sequence |
|---|---|
| C7-SS2-His | MVSDVPRDLEVVAATPTSLLISW[RH]P[HFPT]RYYRCTYGETGGNSPVQECTVP[LQPP]TAT ISGLKPGVDYTITVYAVT[DGRNGRLL]S[I]PISINYRTHHHHHH |
| C7-SS3-His | MVSDVPRDLEVVAATPTSLLISW[RH]P[HFPT]RYYRITCGETGGNSPVQEFTVP[LQPP]TATI SGLKPGVDYTCTVYAVT[DGRNGRLL]S[I]PISINYRTHHHHHH |
| C7-SL1-His | MVSDVPRDCEVVAATPTSLLISW[RH]P[HFPT]RYYRITYGETGGNSPVQEFTVP[LQPP]TATI SGLKPGVDYTITVYAVT[DGRNGRLL]S[I]PICINYRTHHHHHH |
| C7-SL2-His | MVSDVPRDLEVVAATPTSLLISW[RH]P[HFPT]RYYRICYGETGGNSPCQEFTVP[LQPP]TATI SGLKPGVDYTITVYAVT[DGRNGRLL]S[I]PISINYRTHHHHHH |
| C7-SL3-His | MVSDVPRDLEVVAATPTSLLISW[RH]P[HFPT]RYYRITYCETGGNSPCQEFTVP[LQPP]TATI SGLKPGVDYTITVYAVT[DGRNGRLL]S[I]PISINYRTHHHHHH |
| C7-SL4-His | MVSDVPRDLEVVAATPTSLLISW[RH]P[HFPT]RYYRITYGETGGNSPVQEFTVP[LQPP]TATI SGLKPGVCYTITVYAVT[DGRNGRLL]S[I]PISICYRTHHHHHH |
| C7-SL1-LL2-His | MVSDVPRDCEVVAATPTCLLISW[RH]P[HFPT]RYYRITYGETGGNSPVQEFTVP[LQPP]TATI CGLKPGVDYTITVYAVT[DGRNGRLL]S[I]PICINYRTHHHHHH |
| C7-SL1-LL3-His | MVSDVPRDCEVVAATPTSLLISW[RH]P[HFPT]RYYRITYGECGGNSPVQEFTVP[LQPP]TATI SGLKPGVCYTITVYAVT[DGRNGRLL]S[I]PICINYRTHHHHHH |

1. Any one-letter symbol within the box is a mutant amino acid residue relative to protein 10Fn3-WT
2. Any one-letter symbol above the bottom line is a mutant amino acid residue relative to protein C7

Example 2: Protein Production

Protein C7 and its variant protein were expressed in *Escherichia coli*. Briefly, protein C7 and its variant protein were expressed in either a bacterial strain BL21(DE3) pLysS or a bacterial strain SHuffle. The medium for strain BL21 (DE3) pLysS was a LB medium; that for strain SHuffle was a LLB medium.

Firstly, a strain BL21(DE3) pLysS was cultivated in a 5-mL culture medium at 37° C. for 16-18 hours (30° C. for strain SHuffle). The strain BL21(DE3) pLysS was transferred to a 500-mL culture medium, and then cultivated at 37° C. for approximately 4 hours (30° C. and 6 hours for strain SHuffle). After 500 μL-IPTG (the concentration was 1 M) was added, the strain BL21(DE3) pLysS was induced at 25° C. for approximately 16-18 hours to express protein (16° C. and 48 hours for strain SHuffle). After which, the cell pellet was obtained by centrifugation.

Bacteria were dissolved in binding Buffer A (50 mM of sodium phosphate, 300 mM of sodium chloride, pH 7.0) and then were lysed with a French press (the pressure was 1500 psi). After a supernatant was obtained by centrifugation, the supernatant was loaded into a nickel column pre-equilibrated with Buffer A. A target protein was eluted with gradient of elution buffer (300 mM of imidazole in Buffer A, pH 7.0). After elution, glycine SDS-PAGE was performed for protein confirmation. Finally, dialysis with PBS was performed on the obtained recombinant protein, and the recombinant protein was stored at −80° C. until being used.

Example 3: Analysis for Protein Property

Figure 3:
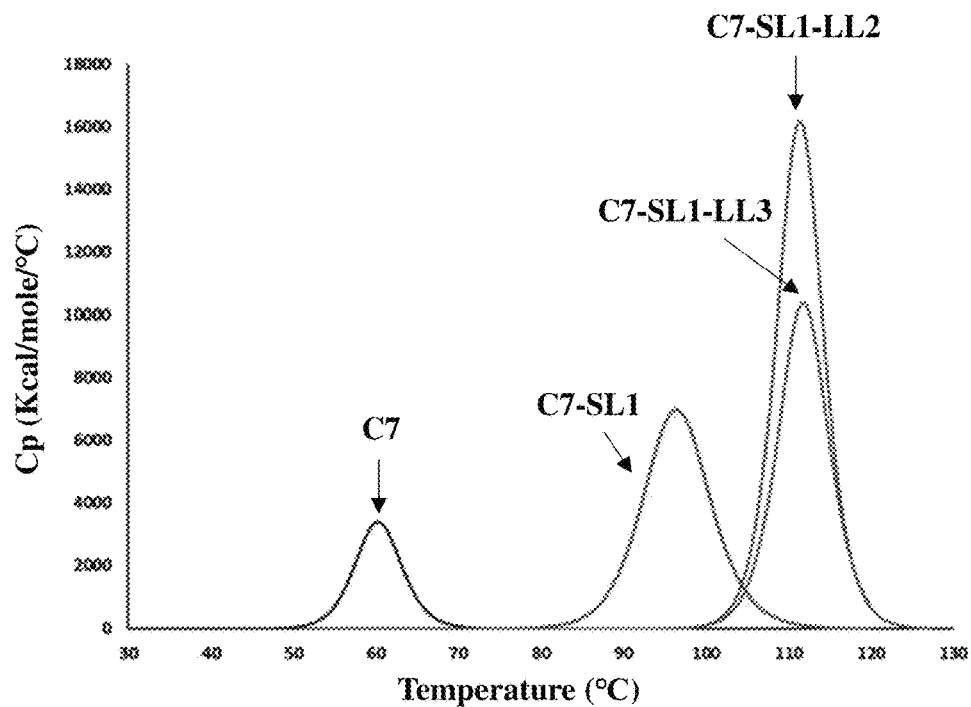
FIG. 3 is a curve chart comparing the melting temperature (Tm) of protein C7 and its variant measured by differential scanning calorimetry (DSC)
Figure 4:
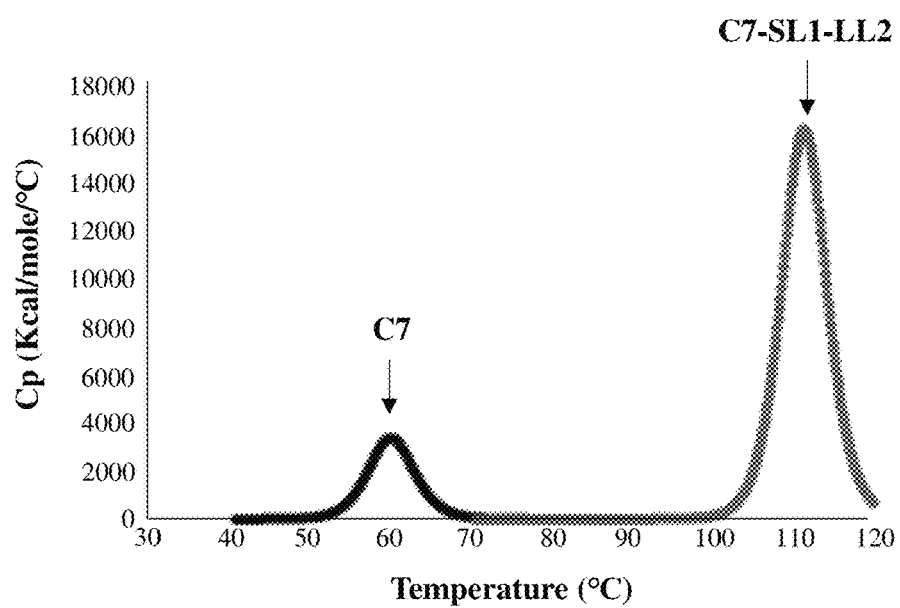
FIG. 4 is a curve chart comparing the melting temperature of protein C7 and protein C7-SL1-LL2 measured by differential scanning calorimetry.
Figure 5:
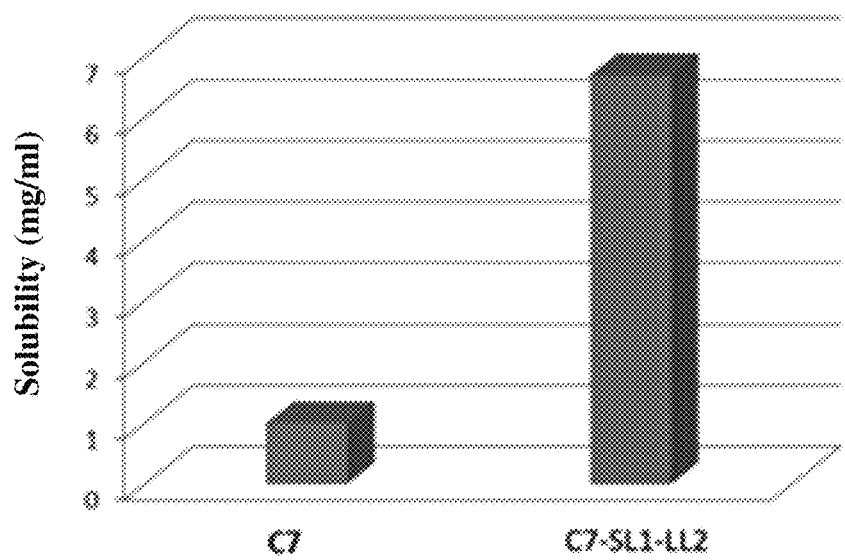
FIG. 5 is a bar chart comparing the solubility of protein C7 and protein C7-SL1-LL2.

Differential scanning calorimetry (DSC) was used to measure the melting temperature of protein. As shown in Table 3 and FIG. 3, the difference in melting temperature between protein C7-SL1 and protein C7 is 37.0° C. higher than that between other protein having a single disulfide bond and protein C7, which implies that protein C7-SL1 has good thermostability. As shown in Table 3 and FIGS. 3-4, protein C7-SL1-LL2 and protein C7-SL1-LL3, each protein obtained by introducing another disulfide bond in protein C7-SL1, have better thermostability.

Ammonium sulfate precipitation was used to measure the protein solubility with reference to J Pharm Sci. 2008 October; 97(10):4155-66. As shown in Table 3, the solubility of protein C7-SL1 in PBS is approximately six times greater than that of protein C7, and also greater than other protein having a single disulfide bond, which indicates that protein C7-SL1 has good solubility. As shown in Table 3, protein C7-SL1-LL2 and protein C7-SL1-LL3, each protein obtained by introducing another disulfide bond in protein C7-SL1, have the solubility in PBS seven times greater than that of protein C7.

Cell proliferation assay was used to analyze the inhibitory activity of protein against human umbilical vein endothelial cell (HUVEC) proliferation. As shown in Table 3, there is no significant difference between the inhibitory activity of protein C7-SL1 against HUVEC proliferation and that of protein C7, which implies that protein C7-SL1 has the ability to inhibit angiogenesis. As shown in Table 3, protein C7-SL1-LL2 and protein C7-SL1-LL3, each protein obtained by introducing another disulfide bond in protein C7-SL1, have inhibitory activity against HUVEC proliferation not significantly different from that of protein C7. This implies protein C7-SL1-LL2 and protein C7-SL1-LL3 also have the ability to inhibit angiogenesis.

Figure 6:
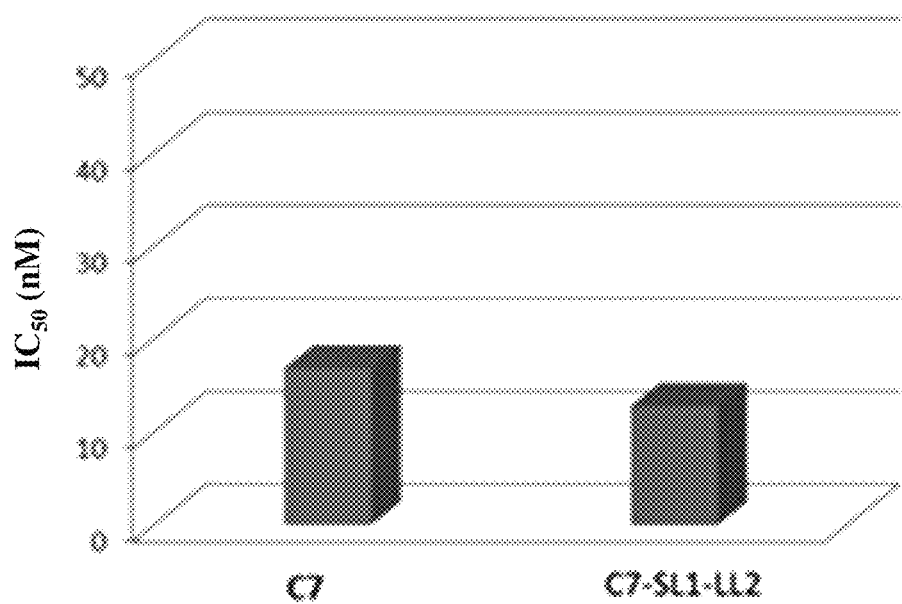
FIG. 6 is a bar chart comparing the affinity of protein C7 and protein C7-SL1-LL2 for VEGFR2 measured by the enzyme-linked immunosorbent assay (ELISA).

Enzyme-linked immunosorbent assay (ELISA) was used to analyze the affinity of protein to vascular endothelial growth factor receptor 2. As shown in Table 3, there is no significant difference between the affinity of protein C7-SL1 to vascular endothelial growth factor receptor 2 and that of protein C7, which implies that protein C7-SL1 has the ability to bind to vascular endothelial growth factor receptor 2. As shown in Table 3 and FIG. 6, protein C7-SL1-LL2 and protein C7-SL1-LL3, each protein obtained by introducing another disulfide bond in protein C7-SL1, have the affinity to vascular endothelial growth factor receptor 2 not significantly different from that of protein C7. Specifically, the affinity of protein C7-SL1-LL2 to vascular endothelial growth factor receptor 2 is slightly greater than that of protein C7. This implies that protein C7-SL1-LL2 and protein C7-SL1-LL3 also have the ability to hind to vascular endothelial growth factor receptor 2.

TABLE 3

| | | | | Thermostability | | Inhibition of HUVEC | Binding affinity to |
|---|---|---|---|---|---|---|---|
| | Site for disulfide bond formation | Yield (mg/L) | Solubility in PBS (mg/mL) | Tm (° C.) | ΔTm (° C.) | proliferation: $IC_{50}$ (nM) | VEGFR2: $IC_{50}$ (nM) |
| C7 | | 34.7 | 1 | 59.3 | 0 | 34.2 ± 6.8 | 16.8 ± 4.4 |
| C7-LL1 | $L9^{loop}/W23^{loop}$ | ND | ND | ND | ND | ND | ND |
| C7-LL2 | $S18^{loop}/S61^{loop}$ | 5.8 | ND | 75.7 | +16.4 | 93.8 ± 20.4 | 18.9 ± 0.9 |
| C7-LL3 | $T40^{loop}/D68^{loop}$ | 10.7 | ND | 76.5 | +17.2 | 73.9 ± 0.0 | 9.8 ± 0.0 |
| C7-LL4 | $K64^{loop}/V67^{loop}$ | 3.5 | ND | ND | ND | 384.9 ± 292.3 | 16.6 ± 3.0 |
| C7-SS1 | $L20^{strand}/T59^{strand}$ | 3.9 | ND | 73.3 | +14.0 | ND | 17.5 ± 1.5 |
| C7-SS2 | $I35^{strand}/F49^{strand}$ | ND | ND | ND | ND | ND | ND |
| C7-SS3 | $Y37^{strand}/I71^{strand}$ | ND | ND | ND | ND | ND | ND |
| C7-SL1 | $L9^{loop}/S90^{strand}$ | 101.0 | 5.9 | 96.3 | +37.0 | 48.6 ± 10.2 | 17.6 ± 2.8 |
| C7-SL2 | $T36^{strand}/V46^{loop}$ | 14.7 | 2.0 | 49.2 | −10.1 | 146.9 ± 0.0 | 17.1 ± 4.2 |
| C7-SL3 | $G38^{strand}/V46^{loop}$ | 12.4 | 2.7 | 71.9 | +12.6 | 115.2 ± 0.0 | 21.3 ± 0.0 |
| C7-SL4 | $D68^{loop}/N92^{strand}$ | 4.5 | ND | 61.6 | +2.3 | 354.0 ± 0.0 | 18.5 ± 4.0 |
| C7-SL1-LL2 | $L9^{loop}/S90^{strand}$, $S18^{loop}/S61^{loop}$ | 15.3 | 6.7 | 111.3 | +52.0 | 52.0 ± 15.1 | 12.8 ± 0.0 |
| C7-SL1-LL3 | $L9^{loop}/S90^{strand}$, $T40^{loop}/D68^{loop}$ | 13.8 | 6.5 | 111.1 | +51.8 | 55.4 ± 8.9 | 19.2 ± 3.5 |

1. ΔTm = (Tm of the test protein) − (Tm of protein C7)
2. ND indicates not detectable because of protein formation in inclusion bodies or not being detected While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A protein, comprising:
a 10th human fibronectin type III domain, wherein the 10th human fibronectin type III domain comprises: an amino acid sequence of SEQ ID No.: 1;
wherein the protein comprises: a mutation to substitute positions 23-31 of SEQ ID No.: 1 with RHPHFPTRY (SEQ ID NO.: 29), a mutation to substitute positions 51-56 of SEQ ID No.: 1 with PLQPPT (SEQ ID NO.: 30), and a mutation to substitute positions 75-87 of SEQ ID No.: 1 with VTDGRNGRLLSIP (SEQ ID NO.: 31);
wherein the protein comprises: a first mutation and a second mutation so that a disulfide bond is formed between a cysteine residue formed by the first mutation and a cysteine residue formed by the second mutation;
wherein the first mutation comprises: a substitution of a leucine residue at position 8 of SEQ ID No.: 1 with the cysteine residue, and the second mutation comprises: a substitution of a tryptophan residue at position 22 of SEQ ID No.: 1 with the cysteine residue;
the first mutation comprises: a substitution of a leucine residue at position 8 of SEQ ID No.: 1 with the cysteine residue, and the second mutation comprises: a substitution of a serine residue at position 89 of SEQ ID No.: 1 with the cysteine residue;
the first mutation comprises: a substitution of a serine residue at position 17 of SEQ ID No.: 1 with the cysteine residue, and the second mutation comprises: a substitution of a serine residue at position 60 of SEQ ID No.: 1 with the cysteine residue;
the first mutation comprises: a substitution of a leucine residue at position 19 of SEQ ID No.: 1 with the cysteine residue, and the second mutation comprises: a substitution of a threonine residue at position 58 of SEQ ID No.: 1 with the cysteine residue;
the first mutation comprises: a substitution of an isoleucine residue at position 34 of SEQ ID No.: 1 with the cysteine residue, and the second mutation comprises: a substitution of a phenylalanine residue at position 48 of SEQ ID No.: 1 with the cysteine residue;
the first mutation comprises: a substitution of a threonine residue at position 35 of SEQ ID No.: 1 with the cysteine residue, and the second mutation comprises: a substitution of a valine residue at position 45 of SEQ ID No.: 1 with the cysteine residue;
the first mutation comprises: a substitution of a tyrosine residue at position 36 of SEQ ID No.: 1 with the cysteine residue, and the second mutation comprises: a substitution of an isoleucine residue at position 70 of SEQ ID No.: 1 with the cysteine residue;
the first mutation comprises: a substitution of a glycine residue at position 37 of SEQ ID No.: 1 with the cysteine residue, and the second mutation comprises: a substitution of a valine residue at position 45 of SEQ ID No.: 1 with the cysteine residue;
the first mutation comprises: a substitution of a threonine residue at position 39 of SEQ ID No.: 1 with the cysteine residue, and the second mutation comprises: a substitution of an aspartate residue at position 67 of SEQ ID No.: 1 with the cysteine residue;
the first mutation comprises: a substitution of a lysine residue at position 63 of SEQ ID No.: 1 with the cysteine residue, and the second mutation comprises: a substitution of a valine residue at position 66 of SEQ ID No.: 1 with the cysteine residue; or
the first mutation comprises: a substitution of an aspartate residue at position 67 of SEQ ID No.: 1 with the cysteine residue, and the second mutation comprises: a substitution of an asparagine residue at position 91 of SEQ ID No.: 1 with the cysteine residue.

2. The protein as claimed in claim 1, wherein the first mutation comprises: a substitution of a leucine residue at position 8 of SEQ ID No.: 1 with the cysteine residue, and the second mutation comprises: a substitution of a tryptophan residue at position 22 of SEQ ID No.: 1 with the cysteine residue.

3. The protein as claimed in claim 1, wherein the first mutation comprises: a substitution of a leucine residue at position 8 of SEQ ID No.: 1 with the cysteine residue, and the second mutation comprises: a substitution of a serine residue at position 89 of SEQ ID No.: 1 with the cysteine residue.

4. The protein as claimed in claim 3, further comprising: a third mutation and a fourth mutation so that a disulfide bond is formed between a cysteine residue formed by the third mutation and a cysteine residue formed by the fourth mutation;
wherein the third mutation comprises: a substitution of a serine residue at position 17 of SEQ ID No.: 1 with the cysteine residue, and the fourth mutation comprises: a substitution of a serine residue at position 60 of SEQ ID No.: 1 with the cysteine residue.

5. The protein as claimed in claim 3, further comprising: a third mutation and a fourth mutation so that a disulfide bond is formed between a cysteine residue formed by the third mutation and a cysteine residue formed by the fourth mutation;

wherein the third mutation comprises: a substitution of a threonine residue at position 39 of SEQ ID No.: 1 with the cysteine residue, and the fourth mutation comprises: a substitution of an aspartate residue at position 67 of SEQ ID No.: 1 with the cysteine residue.

6. The protein as claimed in claim 1, wherein the first mutation comprises: a substitution of a serine residue at position 17 of SEQ ID No.: 1 with the cysteine residue, and the second mutation comprises: a substitution of a serine residue at position 60 of SEQ ID No.: 1 with the cysteine residue.

7. The protein as claimed in claim 1, wherein the first mutation comprises: a substitution of a leucine residue at position 19 of SEQ ID No.: 1 with the cysteine residue, and the second mutation comprises: a substitution of a threonine residue at position 58 of SEQ ID No.: 1 with the cysteine residue.

8. The protein as claimed in claim 1, wherein the first mutation comprises: a substitution of an isoleucine residue at position 34 of SEQ ID No.: 1 with the cysteine residue, and the second mutation comprises: a substitution of a phenylalanine residue at position 48 of SEQ ID No.: 1 with the cysteine residue.

9. The protein as claimed in claim 1, wherein the first mutation comprises: a substitution of a threonine residue at position 35 of SEQ ID No.: 1 with the cysteine residue, and the second mutation comprises: a substitution of a valine residue at position 45 of SEQ ID No.: 1 with the cysteine residue.

10. The protein as claimed in claim 1, wherein the first mutation comprises: a substitution of a tyrosine residue at position 36 of SEQ ID No.: 1 with the cysteine residue, and the second mutation comprises: a substitution of an isoleucine residue at position 70 of SEQ ID No.: 1 with the cysteine residue.

11. The protein as claimed in claim 1, wherein the first mutation comprises: a substitution of a glycine residue at position 37 of SEQ ID No.: 1 with the cysteine residue, and the second mutation comprises: a substitution of a valine residue at position 45 of SEQ ID No.: 1 with the cysteine residue.

12. The protein as claimed in claim 1, wherein the first mutation comprises: a substitution of a threonine residue at position 39 of SEQ ID No.: 1 with the cysteine residue, and the second mutation comprises: a substitution of an aspartate residue at position 67 of SEQ ID No.: 1 with the cysteine residue.

13. The protein as claimed in claim 1, wherein the first mutation comprises: a substitution of a lysine residue at position 63 of SEQ ID No.: 1 with the cysteine residue, and the second mutation comprises: a substitution of a valine residue at position 66 of SEQ ID No.: 1 with the cysteine residue.

14. The protein as claimed in claim 1, wherein the first mutation comprises: a substitution of an aspartate residue at position 67 of SEQ ID No.: 1 with the cysteine residue, and the second mutation comprises: a substitution of an asparagine residue at position 91 of SEQ ID No.: 1 with the cysteine residue.

15. The protein as claimed in claim 1, comprising: an amino acid sequence selected from SEQ ID Nos.: 4-16.

16. A pharmaceutical composition, comprising: a protein as claimed in claim 1; and a pharmaceutically acceptable carrier.

* * * * *

SEQUENCE LISTING

```
Sequence total quantity: 31
SEQ ID NO: 1            moltype = AA  length = 94
FEATURE                 Location/Qualifiers
source                  1..94
                        mol_type = protein
                        organism = Homo sapiens
SEQUENCE: 1
VSDVPRDLEV VAATPTSLLI SWDAPAVTVR YYRITYGETG GNSPVQEFTV PGSKSTATIS   60
GLKPGVDYTI TVYAVTGRGD SPASSKPISI NYRT                              94

SEQ ID NO: 2            moltype = AA  length = 94
FEATURE                 Location/Qualifiers
source                  1..94
                        mol_type = protein
                        organism = synthetic construct
SEQUENCE: 2
VSDVPRDLEV VAATPTSLLI SWRHPHFPTR YYRITYGETG GNSPVQEFTV PLQPPTATIS   60
GLKPGVDYTI TVYAVTDGRN GRLLSIPISI NYRT                              94

SEQ ID NO: 3            moltype = AA  length = 101
FEATURE                 Location/Qualifiers
```

```
                        source          1..101
                                        mol_type = protein
                                        organism = synthetic construct
SEQUENCE: 3
MVSDVPRDLE VVEASPTSIQ ISWRHPHFPT RYYRITYGET GGNSPVQEFT VPLQPPTATI      60
SGLKPGVDYT ITVYAVTDGR NGRLLSIPIS INYRTHHHHH H                          101

SEQ ID NO: 4            moltype = AA   length = 94
FEATURE                 Location/Qualifiers
source                  1..94
                        mol_type = protein
                        organism = synthetic construct
SEQUENCE: 4
VSDVPRDCEV VAATPTSLLI SCRHPHFPTR YYRITYGETG GNSPVQEFTV PLQPPTATIS      60
GLKPGVDYTI TVYAVTDGRN GRLLSIPISI NYRT                                  94

SEQ ID NO: 5            moltype = AA   length = 94
FEATURE                 Location/Qualifiers
source                  1..94
                        mol_type = protein
                        organism = synthetic construct
SEQUENCE: 5
VSDVPRDLEV VAATPTCLLI SWRHPHFPTR YYRITYGETG GNSPVQEFTV PLQPPTATIC      60
GLKPGVDYTI TVYAVTDGRN GRLLSIPISI NYRT                                  94

SEQ ID NO: 6            moltype = AA   length = 94
FEATURE                 Location/Qualifiers
source                  1..94
                        mol_type = protein
                        organism = synthetic construct
SEQUENCE: 6
VSDVPRDLEV VAATPTSLLI SWRHPHFPTR YYRITYGECG GNSPVQEFTV PLQPPTATIS      60
GLKPGVCYTI TVYAVTDGRN GRLLSIPISI NYRT                                  94

SEQ ID NO: 7            moltype = AA   length = 94
FEATURE                 Location/Qualifiers
source                  1..94
                        mol_type = protein
                        organism = synthetic construct
SEQUENCE: 7
VSDVPRDLEV VAATPTSLLI SWRHPHFPTR YYRITYGETG GNSPVQEFTV PLQPPTATIS      60
GLCPGCDYTI TVYAVTDGRN GRLLSIPISI NYRT                                  94

SEQ ID NO: 8            moltype = AA   length = 94
FEATURE                 Location/Qualifiers
source                  1..94
                        mol_type = protein
                        organism = synthetic construct
SEQUENCE: 8
VSDVPRDLEV VAATPTSLCI SWRHPHFPTR YYRITYGETG GNSPVQEFTV PLQPPTACIS      60
GLKPGVDYTI TVYAVTDGRN GRLLSIPISI NYRT                                  94

SEQ ID NO: 9            moltype = AA   length = 94
FEATURE                 Location/Qualifiers
source                  1..94
                        mol_type = protein
                        organism = synthetic construct
SEQUENCE: 9
VSDVPRDLEV VAATPTSLLI SWRHPHFPTR YYRCTYGETG GNSPVQECTV PLQPPTATIS      60
GLKPGVDYTI TVYAVTDGRN GRLLSIPISI NYRT                                  94

SEQ ID NO: 10           moltype = AA   length = 94
FEATURE                 Location/Qualifiers
source                  1..94
                        mol_type = protein
                        organism = synthetic construct
SEQUENCE: 10
VSDVPRDLEV VAATPTSLLI SWRHPHFPTR YYRITCGETG GNSPVQEFTV PLQPPTATIS      60
GLKPGVDYTC TVYAVTDGRN GRLLSIPISI NYRT                                  94

SEQ ID NO: 11           moltype = AA   length = 94
FEATURE                 Location/Qualifiers
source                  1..94
                        mol_type = protein
                        organism = synthetic construct
SEQUENCE: 11
VSDVPRDCEV VAATPTSLLI SWRHPHFPTR YYRITYGETG GNSPVQEFTV PLQPPTATIS      60
GLKPGVDYTI TVYAVTDGRN GRLLSIPICI NYRT                                  94
```

```
SEQ ID NO: 12            moltype = AA   length = 94
FEATURE                  Location/Qualifiers
source                   1..94
                         mol_type = protein
                         organism = synthetic construct
SEQUENCE: 12
VSDVPRDLEV VAATPTSLLI SWRHPHFPTR YYRICYGETG GNSPCQEFTV PLQPPTATIS    60
GLKPGVDYTI TVYAVTDGRN GRLLSIPISI NYRT                                94

SEQ ID NO: 13            moltype = AA   length = 94
FEATURE                  Location/Qualifiers
source                   1..94
                         mol_type = protein
                         organism = synthetic construct
SEQUENCE: 13
VSDVPRDLEV VAATPTSLLI SWRHPHFPTR YYRITYCETG GNSPCQEFTV PLQPPTATIS    60
GLKPGVDYTI TVYAVTDGRN GRLLSIPISI NYRT                                94

SEQ ID NO: 14            moltype = AA   length = 94
FEATURE                  Location/Qualifiers
source                   1..94
                         mol_type = protein
                         organism = synthetic construct
SEQUENCE: 14
VSDVPRDLEV VAATPTSLLI SWRHPHFPTR YYRITYGETG GNSPVQEFTV PLQPPTATIS    60
GLKPGVCYTI TVYAVTDGRN GRLLSIPISI CYRT                                94

SEQ ID NO: 15            moltype = AA   length = 94
FEATURE                  Location/Qualifiers
source                   1..94
                         mol_type = protein
                         organism = synthetic construct
SEQUENCE: 15
VSDVPRDCEV VAATPTCLLI SWRHPHFPTR YYRITYGETG GNSPVQEFTV PLQPPTATIC    60
GLKPGVDYTI TVYAVTDGRN GRLLSIPICI NYRT                                94

SEQ ID NO: 16            moltype = AA   length = 94
FEATURE                  Location/Qualifiers
source                   1..94
                         mol_type = protein
                         organism = synthetic construct
SEQUENCE: 16
VSDVPRDCEV VAATPTSLLI SWRHPHFPTR YYRITYGECG GNSPVQEFTV PLQPPTATIS    60
GLKPGVCYTI TVYAVTDGRN GRLLSIPICI NYRT                                94

SEQ ID NO: 17            moltype = AA   length = 94
FEATURE                  Location/Qualifiers
source                   1..94
                         mol_type = protein
                         organism = synthetic construct
SEQUENCE: 17
VSDVPRDCEV VEASPTSIQI SCRHPHFPTR YYRITYGETG GNSPVQEFTV PLQPPTATIS    60
GLKPGVDYTI TVYAVTDGRN GRLLSIPISI NYRT                                94

SEQ ID NO: 18            moltype = AA   length = 94
FEATURE                  Location/Qualifiers
source                   1..94
                         mol_type = protein
                         organism = synthetic construct
SEQUENCE: 18
VSDVPRDLEV VEASPTCIQI SWRHPHFPTR YYRITYGETG GNSPVQEFTV PLQPPTATIC    60
GLKPGVDYTI TVYAVTDGRN GRLLSIPISI NYRT                                94

SEQ ID NO: 19            moltype = AA   length = 94
FEATURE                  Location/Qualifiers
source                   1..94
                         mol_type = protein
                         organism = synthetic construct
SEQUENCE: 19
VSDVPRDLEV VEASPTSIQI SWRHPHFPTR YYRITYGECG GNSPVQEFTV PLQPPTATIS    60
GLKPGVCYTI TVYAVTDGRN GRLLSIPISI NYRT                                94

SEQ ID NO: 20            moltype = AA   length = 94
FEATURE                  Location/Qualifiers
source                   1..94
                         mol_type = protein
                         organism = synthetic construct
SEQUENCE: 20
VSDVPRDLEV VEASPTSIQI SWRHPHFPTR YYRITYGETG GNSPVQEFTV PLQPPTATIS    60
```

GLCPGCDYTI TVYAVTDGRN GRLLSIPISI NYRT                                        94

SEQ ID NO: 21          moltype = AA   length = 94
FEATURE                Location/Qualifiers
source                 1..94
                       mol_type = protein
                       organism = synthetic construct
SEQUENCE: 21
VSDVPRDLEV VEASPTSIQI SWRHPHFPTR YYRCTYGETG GNSPVQECTV PLQPPTATIS            60
GLKPGVDYTI TVYAVTDGRN GRLLSIPISI NYRT                                        94

SEQ ID NO: 22          moltype = AA   length = 94
FEATURE                Location/Qualifiers
source                 1..94
                       mol_type = protein
                       organism = synthetic construct
SEQUENCE: 22
VSDVPRDLEV VEASPTSIQI SWRHPHFPTR YYRITCGETG GNSPVQEFTV PLQPPTATIS            60
GLKPGVDYTC TVYAVTDGRN GRLLSIPISI NYRT                                        94

SEQ ID NO: 23          moltype = AA   length = 94
FEATURE                Location/Qualifiers
source                 1..94
                       mol_type = protein
                       organism = synthetic construct
SEQUENCE: 23
VSDVPRDCEV VEASPTSIQI SWRHPHFPTR YYRITYGETG GNSPVQEFTV PLQPPTATIS            60
GLKPGVDYTI TVYAVTDGRN GRLLSIPICI NYRT                                        94

SEQ ID NO: 24          moltype = AA   length = 94
FEATURE                Location/Qualifiers
source                 1..94
                       mol_type = protein
                       organism = synthetic construct
SEQUENCE: 24
VSDVPRDLEV VEASPTSIQI SWRHPHFPTR YYRICYGETG GNSPCQEFTV PLQPPTATIS            60
GLKPGVDYTI TVYAVTDGRN GRLLSIPISI NYRT                                        94

SEQ ID NO: 25          moltype = AA   length = 94
FEATURE                Location/Qualifiers
source                 1..94
                       mol_type = protein
                       organism = synthetic construct
SEQUENCE: 25
VSDVPRDLEV VEASPTSIQI SWRHPHFPTR YYRITYCETG GNSPCQEFTV PLQPPTATIS            60
GLKPGVDYTI TVYAVTDGRN GRLLSIPISI NYRT                                        94

SEQ ID NO: 26          moltype = AA   length = 94
FEATURE                Location/Qualifiers
source                 1..94
                       mol_type = protein
                       organism = synthetic construct
SEQUENCE: 26
VSDVPRDLEV VEASPTSIQI SWRHPHFPTR YYRITYGETG GNSPVQEFTV PLQPPTATIS            60
GLKPGVCYTI TVYAVTDGRN GRLLSIPISI CYRT                                        94

SEQ ID NO: 27          moltype = AA   length = 94
FEATURE                Location/Qualifiers
source                 1..94
                       mol_type = protein
                       organism = synthetic construct
SEQUENCE: 27
VSDVPRDCEV VEASPTCIQI SWRHPHFPTR YYRITYGETG GNSPVQEFTV PLQPPTATIC            60
GLKPGVDYTI TVYAVTDGRN GRLLSIPICI NYRT                                        94

SEQ ID NO: 28          moltype = AA   length = 94
FEATURE                Location/Qualifiers
source                 1..94
                       mol_type = protein
                       organism = synthetic construct
SEQUENCE: 28
VSDVPRDCEV VEASPTSIQI SWRHPHFPTR YYRITYGECG GNSPVQEFTV PLQPPTATIS            60
GLKPGVCYTI TVYAVTDGRN GRLLSIPICI NYRT                                        94

SEQ ID NO: 29          moltype = AA   length = 9
FEATURE                Location/Qualifiers
source                 1..9
                       mol_type = protein
                       organism = synthetic construct -continued

```
SEQUENCE: 29
RHPHFPTRY                                                                        9

SEQ ID NO: 30           moltype = AA   length = 6
FEATURE                 Location/Qualifiers
source                  1..6
                        mol_type = protein
                        organism = synthetic construct
SEQUENCE: 30
PLQPPT                                                                           6

SEQ ID NO: 31           moltype = AA   length = 13
FEATURE                 Location/Qualifiers
source                  1..13
                        mol_type = protein
                        organism = synthetic construct
SEQUENCE: 31
VTDGRNGRLL SIP                                                                  13
```